US00PP35442P2

(12) United States Plant Patent
Lim

(10) Patent No.: US PP35,442 P2
(45) Date of Patent: Oct. 31, 2023

(54) FLORIBUNDA SHRUB ROSE PLANT NAMED 'ALTORCAPTAIN'

(50) Latin Name: *Rosa hybrida*
Varietal Denomination: ALTorcaptain

(71) Applicant: Altman Specialty Plants Inc, Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/091,731

(22) Filed: Dec. 30, 2022

(51) Int. Cl.
*A01H 5/02* (2018.01)
*A01H 6/74* (2018.01)

(52) U.S. Cl.
USPC ..... Plt./105

(58) Field of Classification Search
USPC ..... Plt./105, 106, 146, 147
CPC ... A01H 5/02; A01H 5/00; A01H 6/74; A01H 6/749
See application file for complete search history.

(56) References Cited

U.S. PATENT DOCUMENTS

PP9,161 P * 6/1995 Harkness ..... Plt./143

* cited by examiner

*Primary Examiner* — June Hwu
(74) *Attorney, Agent, or Firm* — Cassandra Bright

(57) ABSTRACT

A new and distinct cultivar of *Rosa* plant named 'ALTorcaptain' is disclosed, characterized by distinctive fully double red-orange flowers with a lemony fragrance. Plants are vigorous and can be grown on their own roots. Plants are compact, flower continuously and exhibit good resistance to blackspot disease. The new variety is a *Rosa*, normally produced as an outdoor garden or container plant.

1 Drawing Sheet

Latin name of the genus and species: *Rosa hybrida.*
Variety denomination: 'ALTorcaptain'.

BACKGROUND OF THE INVENTION

The new *Rosa* cultivar is a product of a planned breeding program conducted by the inventor, Peter Ping Lim. The objective of the breeding program was to produce vigorous new garden rose varieties with continuous blooming for ornamental commercial applications. The cross resulting in this new variety was made during June of 2016.

The seed parent is an unnamed, unpatented variety *Rosa* orange flowered seedling. The pollen parent is an unnamed, unpatented variety *Rosa* red flowered seedling. The new variety was selected in July of 2017 by the inventor in a group of seedlings resulting from the 2016 crossing, in a nursery in Vista, Calif.

Asexual reproduction of the new cultivar has been performed by vegetative cuttings. This was first performed at a research greenhouse in Vista, Calif. in July of 2017 and has shown that the unique features of this cultivar are stable and reproduced true to type in more than 5 successive generations.

SUMMARY OF THE INVENTION

The cultivar 'ALTorcaptain' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTorcaptain' These characteristics in combination distinguish 'ALTorcaptain' as a new and distinct *Rosa* cultivar:

1. Double flowers composed of rich orange petals.
2. Flower fragrance is a moderate lemon scent.
3. Early prolific blooming.
4. Dark glossy foliage resistant to black spot and powdery mildew diseases.
5. 2×2 ft. compact plant.
6. Plants can be grown on their own roots; grafting is not required.

PARENT COMPARISONS

Plants of the new cultivar 'ALTorcaptain' are similar to plants of the seed parent, in most horticultural characteristics, however, plants of the new cultivar 'ALTorcaptain' differ in the following:

1. Flowers of the new cultivar are a deeper red color than flowers of the seed parent.
2. Petal count of the new variety is higher than that of the seed parent.
3. Plant size of the new variety is smaller than that of the seed parent.

Plants of the new cultivar 'ALTorcaptain' are similar to plants of the pollen parent in most horticultural characteristics, however, plants of the new cultivar 'ALTorcaptain' differs in the following;

1. Flower color of the new variety is orange; flower color of the pollen parent is red.

COMMERCIAL COMPARISONS

Plants of the new cultivar 'ALTorcaptain' can be compared to the commercial variety *Rosa* 'HARwelcome', U.S.

Plant Pat. No. 9,161. These varieties are similar in most horticultural characteristics, however 'ALTorcaptain' differs in the following:

1. Flowers of the new variety are smaller than flowers of this comparator.
2. Plants of the new variety are smaller and more compact than plants of this comparator.

Plants of the new cultivar 'ALTorcaptain' can also be compared to the commercial variety *Rosa* 'KORconvent', U.S. Plant Pat. No. 25,290. These varieties are similar in most horticultural characteristics, however 'ALTorcaptain' differs in the following:

1. Flowers of the new variety produce about 25 petals, while flowers of this comparator produce about 30 petals.
2. Flowers of the new variety are a bright red-orange color, while flowers of this comparator are a soft apricot-orange color.
3. Plants of the new variety are smaller than plants of this comparator.

BRIEF DESCRIPTION OF THE PHOTOGRAPH

The accompanying photograph illustrates in full color a close up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'ALTorcaptain' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTorcaptain'.

Market classification: Floribunda shrub rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Compact.

Container size: 2 gallon.

Height: 32 cm.

Plant spread: 40 cm.

Rootstock: Own root.

Growth rate: Moderate.

Branching characteristics: Sympodial branching.

Length of primary lateral branches: Average range 8 to 12 cm.

Diameter of lateral branches: Approximately 5 mm to 6 mm.

Quantity branches: 6 to 8 main branches, moderate lateral branches, 10 to 20 lateral branches per main branch.

Branches-young wood:

*Diameter*.—Approximately 4 mm.

*Texture*.—Glabrous, very dense soft, short thorns. Infrequent long thorns.

*Approximately density/quantity of prickles*.—Dense.

*Color*.—Near RHS Green 143B. Anthocyanin coloration not present.

Branches-old wood:

*Diameter*.—Approximately 5 to 9 mm.

*Color*.—Near RHS Greyed-Purple N187C over Yellow-Green 147A.

*Texture*.—Slightly scaly.

*Thorns*.—

*Approximately density/quantity of thorns*.—Young growth: Very dense, soft thorns which disappear with maturity. Approximately 1 mm in diameter and 2 to 3 mm long. Colored near RHS Greyed-Orange N172A. Mature growth: Moderately dense, apiculate thorns about 3 mm at base, 5 mm to 7 mm long. Colored near RHS Grey-Brown 199B. Weakly hooked.

FOLIAGE

Leaf:

*Arrangement*.—Alternate and compound.

*Quantity*.—Average 6 to 10 per main branch.

*Internode*.—Average range 2 cm to 6.5 cm.

*Average length*.—Approximately 12.5 cm.

*Average width*.—Approximately 8 cm.

Rachis:

*Average length*.—Approximately 6.0 cm to 7.0 cm.

*Average diameter*.—Approximately 2 mm.

*Color*.—Upper surface: Near RHS Yellow-Green 146A lightly flushed Greyed-Purple 187A. Lower surface: Near RHS Yellow-Green 146C.

*Texture*.—Glabrous all surfaces.

Leaflet:

*Quantity*.—5 or 7 per leaf, most commonly 7.

*Average length*.—Approximately 4 to 5 cm.

*Average width*.—Approximately 3.2 cm.

*Shape of blade*.—Broad ovate.

*Apex*.—Acute to somewhat mucronate.

*Base*.—Broadly rounded.

*Margin*.—Finely serrate. Weakly undulate.

*Appearance of top surface*.—Medium Glossy.

*Appearance of bottom surface*.—Matte.

*Texture of top surface*.—Glabrous.

*Texture of bottom surface*.—Glabrous.

*Color*.—Young foliage upper side: Near RHS Yellow-Green 144A, lightly flushed Greyed-Purple 187C along margin. Young foliage under side: Near RHS Yellow-Green 144B, heavily flushed Greyed-Purple 184B. Mature foliage upper side: Near RHS Green 137A flushed Greyed-Purple 187B at veins and margin. Mature foliage under side: Near RHS Green 137C, flushed Greyed-Purple 184B.

*Venation*.—Type: Reticulate. Venation color upper side: Near RHS Greyed-Purple 187B. Venation color under side: Near RHS Green 138B.

Petiole:

*Average length*.—Approximately 1.5 cm to 3.0 cm.

*Average diameter*.—Approximately 3 mm.

*Color*.—Upper surface: Near RHS Green 137B lightly flushed Greyed-Purple 187C. Lower surface: Near RHS Green 137C.

*Petiole wing*.—Typically 15 mm long and 7 mm wide. Apex apiculate. Upper surface colored near RHS Green 143C, lower surface colored near Green 143B.

*Texture*.—Glabrous.

FLOWER

Natural flowering season: Spring until Autumn.

Inflorescence type and habit: 3 to 5 flowers typically clustered together.

Rate of flower opening: Approximately 7 days from bud to fully opened flower.

Flower longevity on plant: 10 to 14 days, after fully opened.

Quantity of flowers: 20 to 30 fully opened flowers and buds.

Flower description: Fully double rotate.

Flower shape:

*From above*.—Round to very slightly irregular round.

*Profile of upper part of flower*.—Flattened convex.

*Profile of lower part of flower*.—Flattened convex.

Flower size:

*Diameter*.—Approximately 5 cm to 6 cm.

*Height*.—Approximately 3.2 cm.

Peduncle:

*Length*.—2.0 cm.

*Diameter*.—3 mm.

*Color*.—Near RHS Green 143C.

*Texture*.—Prickly.

Petals:

*Petal arrangement*.—Multiple rotate, overlapping whorls.

*Petal quantity*.—Average 25.

*Length*.—2.5 cm.

*Width*.—2.5 cm.

*Shape*.—Broad deltate to nearly cordate.

*Margin*.—Entire.

*Apex*.—Rounded, irregular, short notches at apex.

*Base*.—Very broad attenuate.

*Texture*.—Glabrous all surfaces.

*Reflexing over time*.—Petals reflex moderately over time.

*Color*.—When opening: Upper surface: Near RHS Orange-Red 33A. Very small basal blotch near Orange-Red 33D. Lower surface: Near RHS Red 40C. Very small basal blotch near Red 49D. Fully opened. Upper surface: Near RHS Red 40C. Very small basal blotch near Red 39D. Lower surface: Near RHS Red 39A. Very small basal blotch near Red 49D. Color changes when aging: Upper surface: Near RHS Red 39B. Very small basal blotch near Red 49D. Lower surface: Near RHS Red 40B. Very small basal blotch near Red 49D.

Bud:

*Shape*.—Ovate.

*Length*.—Approximately 2.5 cm.

*Diameter*.—Approximately 1.5 cm.

*Color*.—Near RHS Red 41A.

Sepals:

*Quantity*.—5.

*Length*.—1.8 cm.

*Width*.—7 mm.

*Shape*.—Deltoid.

*Apex*.—Acute to slightly apiculate. Sepal extensions absent.

*Margin*.—Entire.

*Texture*.—Pubescent lower surface, glabrous upper surface.

*Color*.—Interior Surface: Near RHS Green 138C flushed 138B. Exterior Surface: Near RHS Green 138B blotched Greyed-Purple 187C.

Receptacle:

*Length*.—9 mm.

*Width*.—8 mm.

*Shape*.—Flat.

*Color*.—Near RHS Green 144C.

*Fragrance*.—Moderate lemon scent.

REPRODUCTIVE ORGANS

Stamens:

*Quantity*.—About 80.

*Filament length*.—Approximately 3 mm to 4 mm.

*Filament color*.—Near RHS Greyed-Orange 177D.

Anthers:

*Length*.—2 mm.

*Shape*.—Narrow globular.

*Color*.—Near RHS Greyed-Orange 177A.

*Pollen*.—Color: Near RHS Greyed-Orange 177A. Quantity: Scant or none.

Pistil: Not observed.

OTHER CHARACTERISTICS

Seeds and fruits: Not observed.

Disease/pest resistance: Good overall disease resistance to normal pests and diseases typical of garden roses. Very good resistance to blackspot (*Diplocarpon rosae*). Very good resistance to powdery mildew (*Podosphaera pannosa*). In a three-year confidential field trial of floribunda shrub roses the new variety 'AlTorcaptain' remains free of powdery mildew year-round while varieties planted nearby were showed symptoms of powdery mildew.

What is claimed is:

1. A new and distinct cultivar of floribunda shrub rose plant named 'ALTorcaptain' as herein illustrated and described.

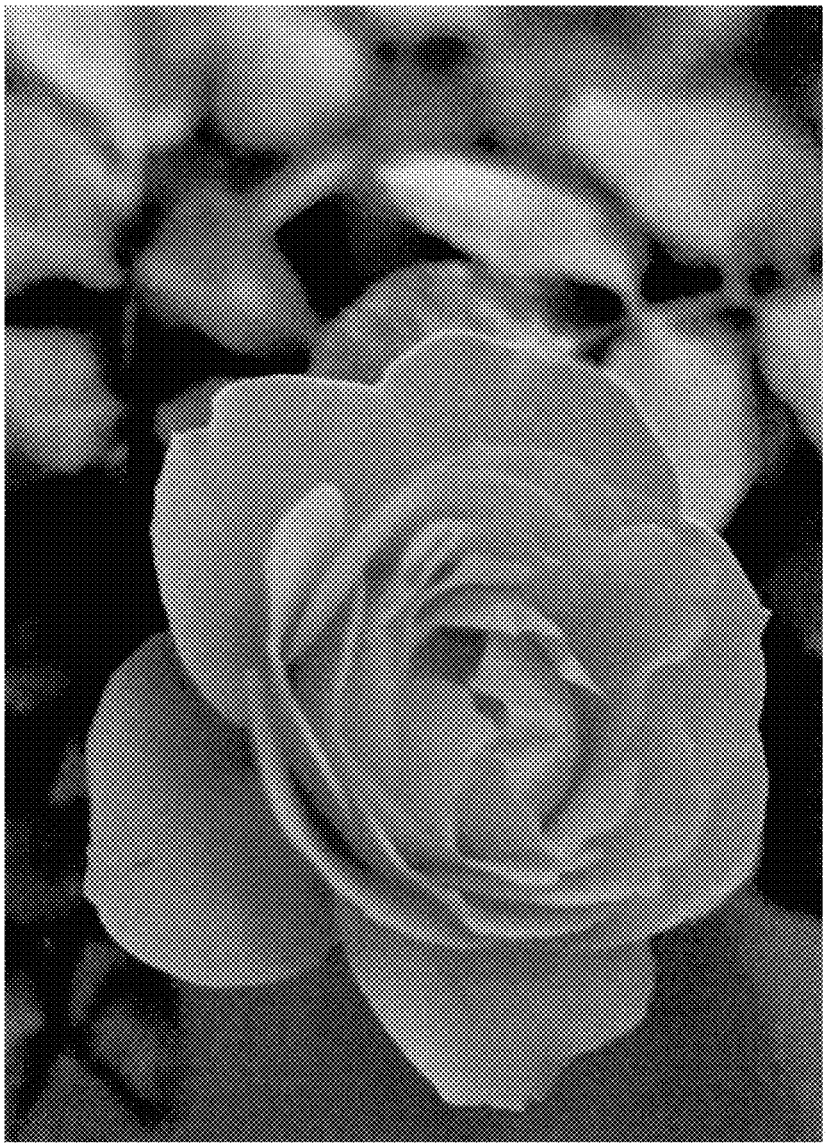

* * * * *